United States Patent [19]

Morris

[11] Patent Number: 4,569,341

[45] Date of Patent: Feb. 11, 1986

[54] SPLIT SHEET SURGICAL DRAPE

[75] Inventor: Henrietta K. Morris, Arlington, Tex.

[73] Assignee: Surgikos, Inc., Arlington, Tex.

[21] Appl. No.: 604,110

[22] Filed: Apr. 26, 1984

[51] Int. Cl.[4] .............................................. A61F 13/00
[52] U.S. Cl. ............................... 128/132 D; 2/DIG. 7
[58] Field of Search ........................... 128/132, 132 D;
2/DIG. 7, 114, 125; 383/7, 9, 10

[56] References Cited

U.S. PATENT DOCUMENTS 3,882,859 5/1975 Ericson ........................... 128/132 D
3,926,185 12/1975 Krzewinski ..................... 128/132 D
3,930,497 1/1976 Krebs et al. .................... 128/132 D
4,041,942 8/1977 Dougan et al. ................. 128/132 D

*Primary Examiner*—Gene Mancene
*Assistant Examiner*—John G. Weiss
*Attorney, Agent, or Firm*—Michael Q. Tatlow

[57] ABSTRACT

A split sheet surgical drape is disclosed. The opening in the drape has a plastic border between one and six inches in width on both surfaces of the drape. The lower surface of the border is coated with adhesive. The plastic border provides better attachment of the drape to similar drapes when the drapes are in use.

3 Claims, 8 Drawing Figures

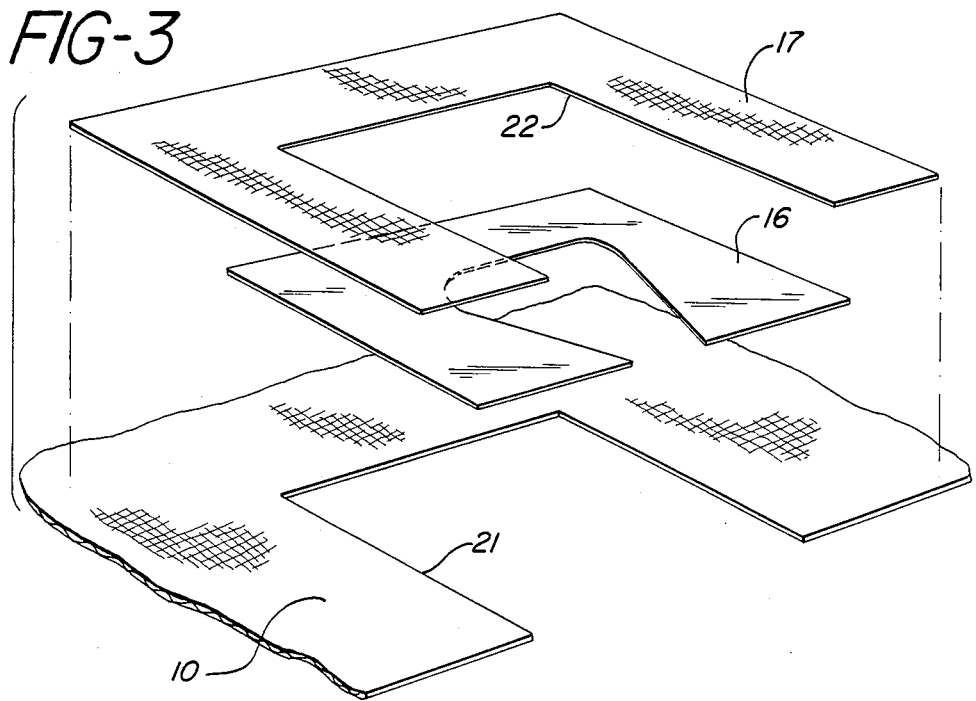
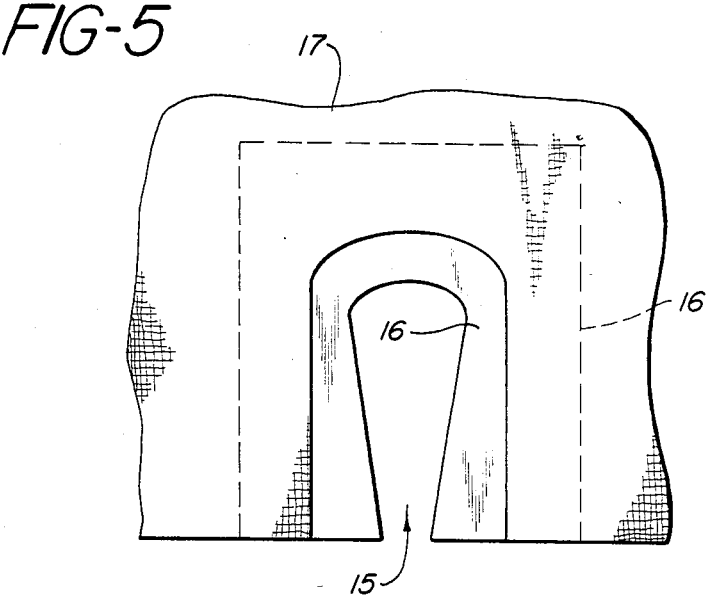

SPLIT SHEET SURGICAL DRAPE

FIELD OF THE INVENTION

The present invention relates to surgical drapes and, particularly, to surgical drapes of the type that are used to drape limbs. The drape of the present invention provides greater security in the placement of the drape around the limb of the patient prior to the surgical procedure.

BACKGROUND OF THE INVENTION

Prior Art

Specially designed surgical drapes for draping the limbs of patients have been in use for some time. U.S. Pat. No. 3,910,268 discloses a surgical drape for use in orthopaedic and related surgery which is a sheet with a slit in the sheet to fit aroung the limb of a patient. The drape contains a flap which can be used to completely surround the limb of the patient after the limb is inserted through the drape.

U.S. Pat. No. 3,926,185 also discloses a surgical drape for use in orthopaedic procedures. The drape is a split sheet with one or two flaps which may be used to totally surround the limb of the patient extending through the drape.

U.S. Pat. No. 3,791,381 discloses a surgical drape which can be formed into a split sheet by cutting the drape from one edge of the drape towards the center.

These prior art surgical drapes, although they were effective in draping a patient, required some mechanism to secure the drape in the proper position around the patient's limbs. This could be towel clamps or other clamps which are commonly used in surgical procedures to secure drapes in place. Another technique for securing drapes in position is the use of adhesive strips which can be used directly on the surface of two adjacent drapes to secure the drapes together.

The above-mentioned drapes all had limitations in that the use of towel clamps or clips had a tendency to perforate the drape, which would allow liquids present in the operating room to penetrate the drape and possibly contaminate the patient. The use of adhesive strips, although overcoming the problems of the clamps or clips, were inadequate to hold the drape in place because the adhesive would not securely bond to the fibrous surface of the drape.

THE PRESENT INVENTION

The present invention provides a split sheet surgical drape which can be easily secured in position around the limb of a patient. Generally, two such drapes are used, and the patient is draped from either side of the limb and the drapes secured together to isolate the limb on which the surgical procedure will be performed from the rest of the body of the patient. In the present drape, there is a plastic film around the opening in the drape which provides a better surface for the application of adhesive to hold the drapes in position on the patient.

DETAILED DESCRIPTION OF THE DRAWINGS

The drape of the present invention can be more clearly understood with reference to the following drawings in which:

FIG. 3 is an exploded view of the fenestration or opening in the drape of the present invention showing the preferred method of assembling the drape.

FIG. 5 is a detailed view of a portion of the drape shown in FIG. 3 after assembly.

DETAILED DESCRIPTION OF THE PRESENT INVENTION

Figure 1:
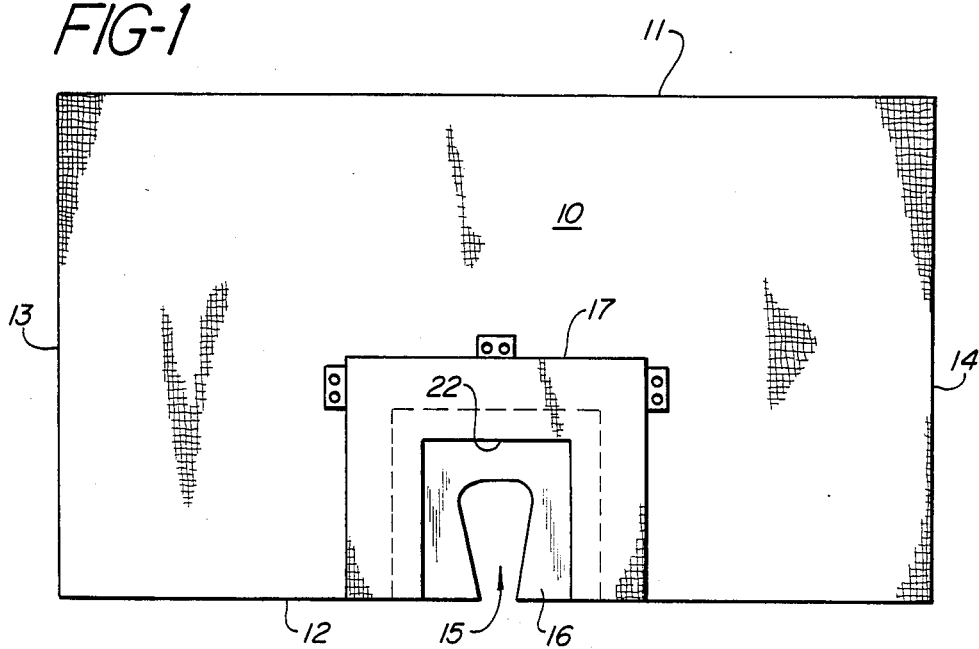
FIG. 1 is a top plan view of one of the embodiments of the drape of the present invention.

As shown in FIG. 1, the drape of the present invention comprises a main drape sheet 10 which has a top edge 11, a bottom edge 12 and two opposing side edges 13 and 14. The drape may be constructed of a nonwoven fabric of the type commonly used in the manufacture of single-use surgical drapes. Such fabrics are usually treated with a water-repellent finish and may be treated with a fire-retardant composition. There is an opening or fenestration 15 at one edge of the main drape sheet. As shown in the present FIG. 1, the opening is at the bottom edge of the sheet, but it could be placed at any of the edges of the sheet including the side edges. There is a reinforcement area 17 which surrounds the opening 15. The reinforcement area is usually an additional layer of nonwoven fabric with a coextensive layer of impervious plastic film on its lower surface. The reinforcement area provides greater resistance to penetration of instruments and prevents the penetration of liquids through the drape at the surgical site. There are tube tabs which can be bent upwardly from the edge of the reinforcement area to secure electrocauteries and other surgical tubing to the sheet. In the present drape there is a border of plastic material which extends beyond the end of the reinforcement area and which is secured to either side of the drape or between the reinforcement area and the main sheet of the drape. The border of plastic material should be at least one inch in width and may be up to six inches in width.

Figure 2:
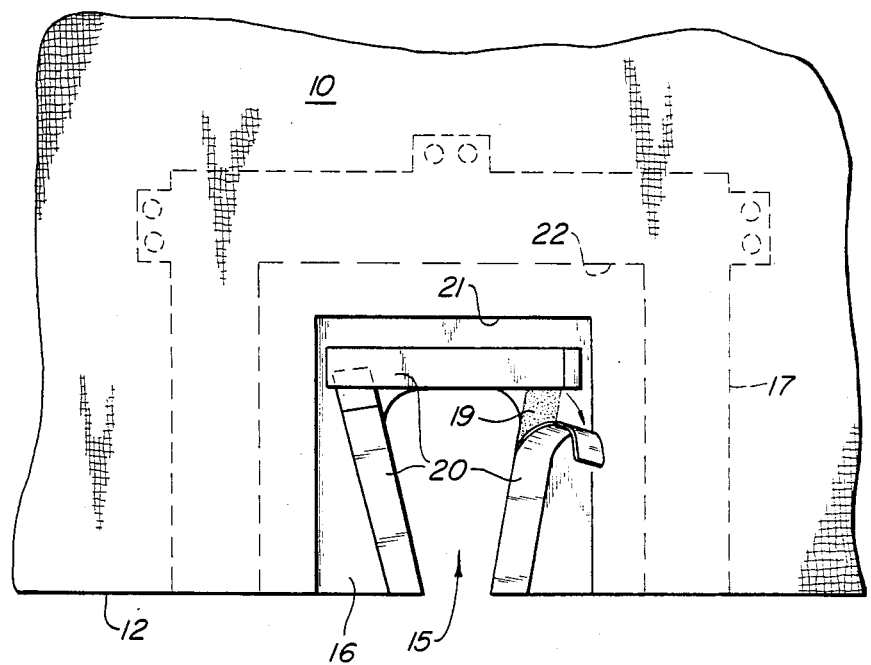
FIG. 2 is a detailed view of the lower surface of the drape of FIG. 1 showing the adhesive on the drape.

As shown in FIG. 2, on the bottom of the drape there is an adhesive 19 surrounding at least the portion of the opening 15. The adhesive can be applied in the form of double-faced tape or may be coated directly on the plastic film. In FIG. 2, the adhesive is shown on all three sides of the opening, which is the preferred construction, but it should be understood that it need not be on all three sides of the opening. There is a release cover 20 over the adhesive, which is removed immediately before the adhesive is applied to a patient.

In FIG. 3 there is shown the preferred method of making the drape of the present invention. The main sheet 10 is shown with a cutout portion 21 which corresponds to a cutout portion 22 in the reinforcement portion of the drape 17. There is a plastic insert 16, which is larger than the cutout portions 21 or 22, which is adhesively secured or heat sealed to the main body of the drape and to the reinforcement area. The resulting configuration is shown in FIG. 5. The dotted line being the extent of the plastic beneath the upper surface of the drape. The plastic border is exposed on both the upper and lower surfaces of the drape. The particular configuration of the fenestration or opening 15 depends on the intended use of the drape. The configuration in FIG. 1 is particularly useful in shoulder surgery. The closed end of the fenestration is wider than the open end, and the sides of the fenestration converge toward the opening.

Figure 4A:
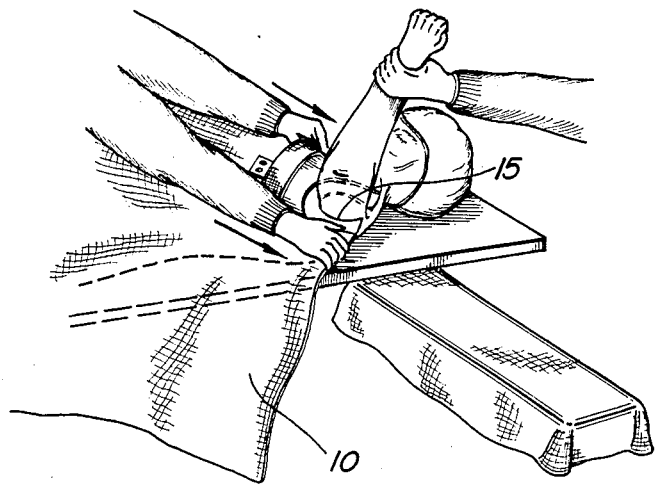
FIGS. 4a and 4b show the application of the drape of the present invention to a patient.
Figure 4B:
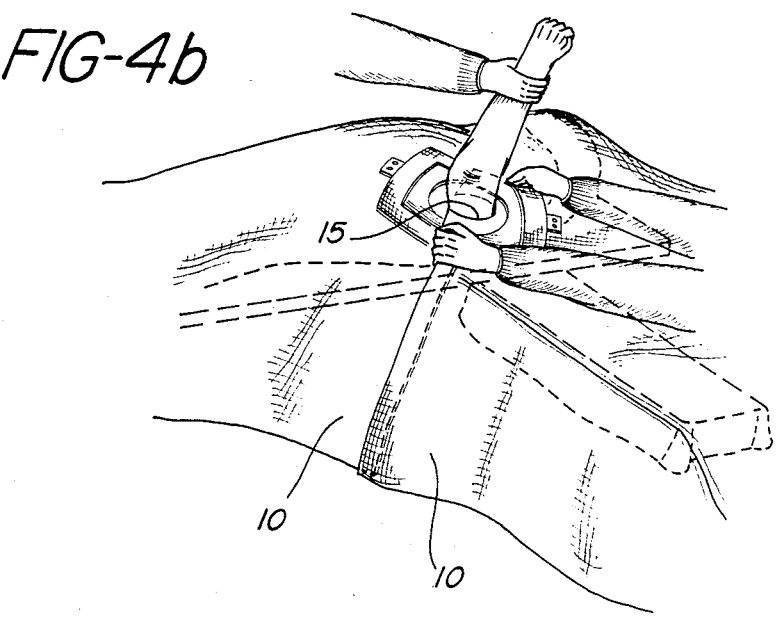

The application of the surgical drape of the present invention to a patient is shown in FIGS. 4a and 4b. In the placement of the drape, the adhesive covers would be removed and the drape secured to the body of the patient as shown in FIG. 4a. The base of the limb of the patient is fitted into the opening 15 of the drape, and the plastic portion of the drape snuggly fits against the base of the limb of the patient. As shown in FIG. 4b, another drape of the same construction as the drape shown in 4a is fitted over the patient's limb from the opposite direction than the drape shown in FIG. 4a. The release sheet over the adhesive would be removed from the drape shown in 4b, and the drape would be adhesively secured to the plastic area around the opening of the drape shown in FIG. 4a.

Figure 6:
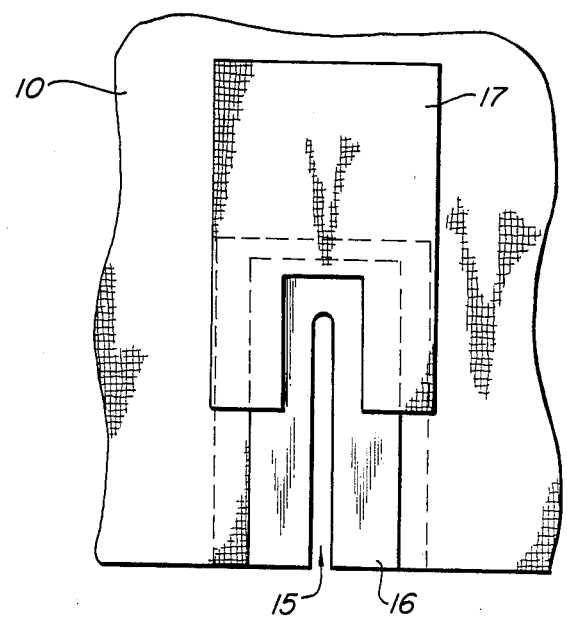
FIG. 6 shows a modification of the drape of the present invention.

FIG. 6 shows a drape similar to that shown in FIG. 1, but the opening 15 is an elongated opening with parallel sides.

Figure 7:
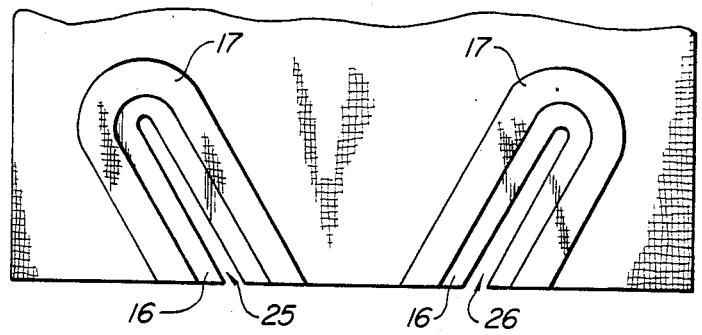
FIG. 7 shows another modification of the drape of the present invention.

The drape shown in FIG. 7 has two openings 25 and 26. This drape would be used in a bilateral procedure in which, for example, both legs of the patient would be operated on at the same time.

The opening shown in FIG. 6 is particularly advantageous for legs; whereas, the opening in FIG. 5, in which the interior or closed end of the opening is wider than the opening at the edge of the sheet, would be more preferred in surgery on a shoulder or arm, as it is more difficult to properly position a surgical drape around the arm to adequately cover the torso of the patient.

I claim:

1. A surgical drape comprising a generally rectangular sheet of a liquid repellent, nonwoven fabric, said sheet having a top edge and a bottom edge and two opposing side edges and an upper surface and a lower surface, at least one opening at one edge of the sheet, the opening commencing at the edge and extending inwardly into the sheet, a plastic border having at least one inch in width around the major portion of the periphery of the opening in said sheet and extending into the opening, an adhesive coating on the lower surface of the plastic border to secure the opening in a position around the limb of a surgical patient, and a release sheet overlying the adhesive coating.

2. The surgical drape of claim 1 in which the width of the opening at its closed end is greater than the width of the opening at the edge of the sheet.

3. The surgical drape of claim 1 in which the plastic border is between one and six inches in width.

* * * * *